(12) United States Patent
Trivedi

(10) Patent No.: US 10,271,865 B2
(45) Date of Patent: Apr. 30, 2019

(54) DEVICES AND METHODS FACILITATING SLEEVE GASTRECTOMY PROCEDURES

(71) Applicant: Covidien LP, Mansfield, MA (US)

(72) Inventor: Amit Trivedi, Upper Saddle River, NJ (US)

(73) Assignee: Covidien LP, Mansfield, MA (US)

( * ) Notice: Subject to any disclaimer, the term of this patent is extended or adjusted under 35 U.S.C. 154(b) by 224 days.

(21) Appl. No.: 15/451,713

(22) Filed: Mar. 7, 2017

(65) Prior Publication Data

US 2017/0172597 A1 Jun. 22, 2017

Related U.S. Application Data

(63) Continuation of application No. 14/055,974, filed on Oct. 17, 2013, now Pat. No. 9,603,735.

(Continued)

(51) Int. Cl.
*A61B 17/30* (2006.01)
*A61F 5/00* (2006.01)
(Continued)

(52) U.S. Cl.
CPC ........ *A61B 17/30* (2013.01); *A61B 17/00234* (2013.01); *A61F 5/0083* (2013.01);
(Continued)

(58) Field of Classification Search
CPC ........ A61B 17/00234; A61B 17/07207; A61B 2017/00292; A61B 2017/00818; A61B 2017/306; A61F 5/0083; A61F 5/0089
See application file for complete search history.

(56) References Cited

U.S. PATENT DOCUMENTS

| 4,328,805 A | 5/1982 | Akopov et al. |
| 5,297,536 A | 3/1994 | Wilk |

(Continued)

FOREIGN PATENT DOCUMENTS

| CN | 1931107 A | 3/2007 |
| CN | 201365906 Y | 12/2009 |

(Continued)

OTHER PUBLICATIONS

Chinese Office Action (with English translation), dated Nov. 16, 2017, corresponding to Chinese Application No. 201380054572.1; 15 total pages.

(Continued)

*Primary Examiner* — Christine H Matthews

(57) ABSTRACT

A device for use in bariatric surgery includes a tube member, a coupling member, and a rod member. The tube member includes a proximal portion and a distal portion having a distal end. The coupling member is affixed to the tube member. The rod member includes a proximal portion and a distal portion having a distal end. The rod member is slidably coupled with the coupling member. The distal end of the rod member is fixedly coupled to the distal end of the tube member. The proximal portion of the rod member is translatable relative to the tube member to transition the distal portion of the rod member between a contracted position, wherein the distal portion of the rod member extends along the distal portion of the tube member, and a deployed position, wherein the distal portion of the rod member bows outwardly relative to the tube member.

6 Claims, 4 Drawing Sheets

Related U.S. Application Data

(60) Provisional application No. 61/716,109, filed on Oct. 19, 2012.

(51) Int. Cl.
*A61B 17/00* (2006.01)
*A61B 17/072* (2006.01)

(52) U.S. Cl.
CPC ...... *A61F 5/0089* (2013.01); *A61B 17/07207* (2013.01); *A61B 2017/00292* (2013.01); *A61B 2017/00725* (2013.01); *A61B 2017/00818* (2013.01); *A61B 2017/00907* (2013.01); *A61B 2017/306* (2013.01); *A61B 2217/005* (2013.01); *A61B 2217/007* (2013.01); *F04C 2270/0421* (2013.01)

(56) References Cited

U.S. PATENT DOCUMENTS

| | | | |
|---|---|---|---|
| 5,382,231 A | 1/1995 | Shlain | |
| 5,401,241 A | 3/1995 | Delany | |
| 5,458,131 A | 10/1995 | Wilk | |
| 5,465,709 A | 11/1995 | Dickie et al. | |
| 5,718,666 A | 2/1998 | Alarcon | |
| 5,913,813 A | 6/1999 | Williams et al. | |
| 7,153,131 B2 | 12/2006 | Crohn | |
| 7,896,894 B2 | 3/2011 | Ortiz et al. | |
| 8,092,378 B2 | 1/2012 | Roth et al. | |
| 8,147,502 B2 | 4/2012 | Albrecht et al. | |
| 8,192,448 B2 | 6/2012 | Bessler et al. | |
| 8,454,503 B2 | 6/2013 | Roth et al. | |
| 8,663,149 B2 | 3/2014 | Gagner et al. | |
| 9,603,735 B2 | 3/2017 | Trivedi | |
| 2004/0006351 A1 | 1/2004 | Gannoe et al. | |
| 2004/0092974 A1 | 5/2004 | Gannoe et al. | |
| 2005/0119674 A1 | 6/2005 | Gingras | |
| 2005/0203489 A1 | 9/2005 | Saadat et al. | |
| 2005/0251158 A1 | 11/2005 | Saadat et al. | |
| 2006/0015151 A1 | 1/2006 | Aldrich | |
| 2006/0106288 A1 | 5/2006 | Roth et al. | |
| 2006/0200004 A1 | 9/2006 | Wilk | |
| 2006/0241344 A1 | 10/2006 | Wilk | |
| 2006/0241570 A1 | 10/2006 | Wilk | |
| 2006/0264689 A1 | 11/2006 | Viole et al. | |
| 2007/0032702 A1 | 2/2007 | Ortiz | |
| 2008/0221384 A1 | 9/2008 | Chi Sing et al. | |
| 2008/0249404 A1 | 10/2008 | Mikkaichi et al. | |
| 2010/0222668 A1 | 9/2010 | Dalke et al. | |
| 2011/0178454 A1 | 7/2011 | Gagner et al. | |
| 2011/0288576 A1 | 11/2011 | Hoffman | |
| 2012/0165608 A1 | 6/2012 | Banik et al. | |
| 2012/0184981 A1 | 7/2012 | Pecor et al. | |
| 2012/0239061 A1 | 9/2012 | Mathur | |
| 2013/0165774 A1 | 6/2013 | Nocca | |
| 2014/0018722 A1 | 1/2014 | Scott et al. | |

FOREIGN PATENT DOCUMENTS

| | | | |
|---|---|---|---|
| CN | 102626536 A | 8/2012 | |
| ES | 2326937 A1 | 10/2009 | |
| JP | 2008-161686 A | 7/2008 | |
| JP | 3178309 U | 9/2012 | |
| WO | 02096327 A2 | 12/2002 | |
| WO | 2008121409 A1 | 10/2008 | |
| WO | 2009097585 A1 | 8/2009 | |
| WO | 2012138737 A1 | 10/2012 | |
| WO | 2014062881 A1 | 4/2014 | |

OTHER PUBLICATIONS

Australian Examination Report 1 dated Oct. 31, 2017, corresponding to Austrailian Application No. 2013331242; 4 pages.

Japanese Final Office Action dated Dec. 7, 2017 in corresponding Japanese Patent Application No. 2015-537811 with English translation, 8 pages.

European Search Report, dated Mar. 19, 2015, corresponding to European Application No. 14192226.0; 7 pages.

European Search Report, dated Mar. 24, 2015, corresponding to European Application No. 14192416.7; 7 pages.

Dietel et al., "Endoscopy of Vertical Banded Gastroplasty," The American Surgeon, May 1989, vol. 55; pp. 287-890.

Dietel et al., "Vertical Banded Gastroplasty: Results in 233 Patients," The Canadian Journal of Surgery, Sep. 1986, vol. 29, No. 5; pp. 322-324.

Mason et al., "Vertical Gastroplasty: Evolution of Vertical Banded Gastroplasty," World Journal of Surgery, Sep. 1998, vol. 22, No. 9; pp. 919-924.

Extended European Search Report dated Sep. 17, 2015, corresponding to European Patent Application 15167339.9; 10 pages.

Extended European Search Report dated Oct. 1, 2015, corresponding to European Application No. 15167342.3; 7 pages.

Supplementary European Search Report dated Sep. 22, 2016 in corresponding European Patent Application No. 13847139, 6 pages.

Chinese Office Action dated Sep. 23, 2016 in corresponding Chinese Patent Application No. 201380054572.1 with English translation, 17 pages.

Japanese Office Action dated Jun. 29, 2017 issued in corresponding Japanese Patent Application No. 2015-537811.

Chinese Office Action dated May 2, 2017 in corresponding Chinese Patent Application No. 201380054572.1 together with English translation, 16 pages.

DEVICES AND METHODS FACILITATING SLEEVE GASTRECTOMY PROCEDURES

CROSS-REFERENCE TO RELATED APPLICATIONS

This application is a continuation of U.S. patent application Ser. No. 14/055,974, filed Oct. 17, 2013, which claims the benefit of and priority to U.S. Provisional Patent Application Ser. No. 61/716,109, filed on Oct. 19, 2012, the entire contents of which are incorporated herein by reference.

BACKGROUND

Technical Field

The present disclosure relates generally to bariatric surgery and, more particularly, to devices and methods that facilitate performing sleeve gastrectomy procedures.

Background of Related Art

Obesity is reaching epidemic proportions in many regions of the world, particularly in the United States. In order to treat obesity, various surgical procedures have been developed including, for example, gastric bypass, adjustable gastric banding, and sleeve gastrectomy. The goal in each of these procedures is to reduce the patient's stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting the stomach, e.g., using a stapling device or other suitable device, to reduce the patient's stomach volume. Sleeve gastectomy procedures are often aided by the use of a bougie, which serves as a guide or template for transecting the stomach to the appropriate configuration while inhibiting inadvertent transection of stomach or esophageal tissue. Once the stomach has been appropriately transected, the bougie is removed and a leak test is performed to determine whether there are any areas of extravasation.

There is a need for a device and/or method of positioning the stomach, or other hollow organ, to avoid shifting of the sides of the organ with respect to one another during transection, stapling etc., in a surgical procedure. There is a need for a simpler, more convenient way to perform a leak test, visualize the transected tissue, etc.

SUMMARY

In an aspect of the present disclosure, a medical device comprises a flexible tube that is hollow and contains a channel extending from a proximal opening to a distal closed tapered end, a series of perforations or openings towards the distal end of the tube allowing for suction fixation of tissue a flexible component alongside the tube that when deployed allows for the stretching of a stomach to its original shape, the application of suction placing the tube along a lesser curvature of the stomach, fixing anterior and posterior walls of the stomach, and preventing their movement while the surgeon transects the stomach, the suction allowing for clear identification of the tube.

The flexible component is desirably an attached movable element. The tube can be made of silicone. A coupling device that holds the movable element to the tube can be provided. The movable element can be deployable to align the stomach by evening out the anterior and posterior walls of the stomach and by pushing the tube and a perforated area of the tube towards the lesser curvature of the stomach. Suction can be applied at a proximal end of the tube. Air or colored fluid can be instilled into a proximal end of the tube.

In a further aspect, a device for use in bariatric surgery provided in accordance with the present disclosure generally includes an elongated flexible tube member, a coupling member, and an elongated resilient rod member. The tube member defines a proximal portion and a distal portion having a distal end. The coupling member is affixed to the tube member intermediate the proximal and distal portions of the tube member. The rod member defines a proximal portion and a distal portion having a distal end. The rod member is slidably coupled to the coupling member intermediate the proximal and distal portions of the rod member. The distal end of the rod member is fixedly coupled to the distal end of the tube member. The proximal portion of the rod member is translatable relative to the tube member to transition the distal portion of the rod member between a contracted position, wherein the distal portion of the rod member extends along the distal portion of the tube member, and a deployed position, wherein the distal portion of the rod member bows outwardly relative to the tube member.

In embodiments, the tube member defines a lumen extending therethrough and the distal portion of the tube member defines a plurality of apertures in fluid communication with the lumen.

In embodiments, a suction source is provided. The suction source is operably coupled to the tube member and configured to apply suction to the lumen of the tube member.

In embodiments, a fluid source is provided. The fluid source is operably coupled to the tube member and configured to supply fluid to the lumen of the tube member.

In embodiments, an end cap is affixed to the distal end of the tube member. The distal end of the rod member is affixed to the end cap. Further, the distal end of the rod member may be monolithically formed with the end cap. The cap can house a releasable connection of the rod member and tube member, or other mechanisms.

In embodiments, in the deployed position, the distal portion of the rod member defines a curvature complementary to a greater curvature portion of a patient's stomach.

In embodiments, the coupling member includes a ring disposed about the tube member. The ring slidably receives the rod member.

Also provided in accordance with the present disclosure is a system for use in bariatric surgery. The system includes a device having an elongated flexible tube member, a coupling member, and an elongated resilient rod member. The tube member includes a lumen extending therethrough and defines a proximal portion and a distal portion having a distal end. The distal portion of the tube member defines a plurality of apertures therethrough in fluid communication with the lumen. The coupling member is affixed to the tube member intermediate the proximal and distal portions of the tube member. The rod member defines a proximal portion and a distal portion having a distal end. The rod member is slidably coupled with the coupling member intermediate the proximal and distal portions of the rod member. The distal end of the rod member is fixedly coupled to the distal end of the tube member. The proximal portion of the rod member is translatable relative to the tube member to transition the distal portion of the rod member between a contracted position, wherein the distal portion of the rod member extends along the distal portion of the tube member, and a deployed position, wherein the distal portion of the rod member bows outwardly relative to the tube member. The system further includes a suction source and a fluid source.

The suction source is operably coupled to the tube member and configured to apply suction to the lumen for suctioning stomach contents through the apertures and into the lumen and/or for suctioning stomach tissue to the distal portion of the tube member. The fluid source is operably coupled to the tube member and configured to supply fluid to the tube member for delivery to a patient's stomach via the plurality of apertures.

In embodiments, the device further includes an end cap affixed to the distal end of the tube member. The distal end of the rod member is affixed to the end cap. The system end cap may further be configured to seal the lumen at the distal end of the tube member. The distal end of the rod member may be monolithically formed with the end cap.

In embodiments, in the deployed position, the distal portion of the rod member defines a curvature complementary to a greater curvature portion of a patient's stomach.

In embodiments, one or more control members is provided for controlling a suction pressure applied by the suction source and/or controlling a flow rate of fluid provided from the fluid source.

A method of bariatric surgery provided in accordance with the present disclosure includes inserting a device, e.g., a device similar to any of the embodiments detailed above, at least partially into a patient's stomach and transitioning the device from a contracted condition to a deployed condition. In the deployed condition, the distal portion of the rod member bows outwardly relative to the tube member to complementarily mate with a greater curvature portion of the patient's stomach. The method further includes applying suction to retain a lesser curvature portion of the patient's stomach in complementary mating relation with the distal portion of the tube member, transitioning the device from the deployed condition back to the contracted condition, and transecting the patient's stomach adjacent the tube member.

In embodiments, the proximal portion of the rod member is translated distally relative to the tube member to transition the device from the contracted condition to the deployed condition. In embodiments, the proximal portion of the rod member is translated proximally relative to the tube member to transition the device from the deployed condition back to the contracted condition.

In embodiments, the method further includes introducing fluid through the tube member and into the patient's stomach to perform a leak test.

In embodiments, transecting the patient's stomach includes transecting the patient's stomach to form a tubular structure disposed about the distal portion of the tube member and having a diameter similar to a diameter of the distal portion of the tube member.

BRIEF DESCRIPTION OF THE DRAWINGS

Various aspects and features of the present disclosure are described herein with reference to the drawings wherein.

DETAILED DESCRIPTION OF EMBODIMENTS

Figure 1:
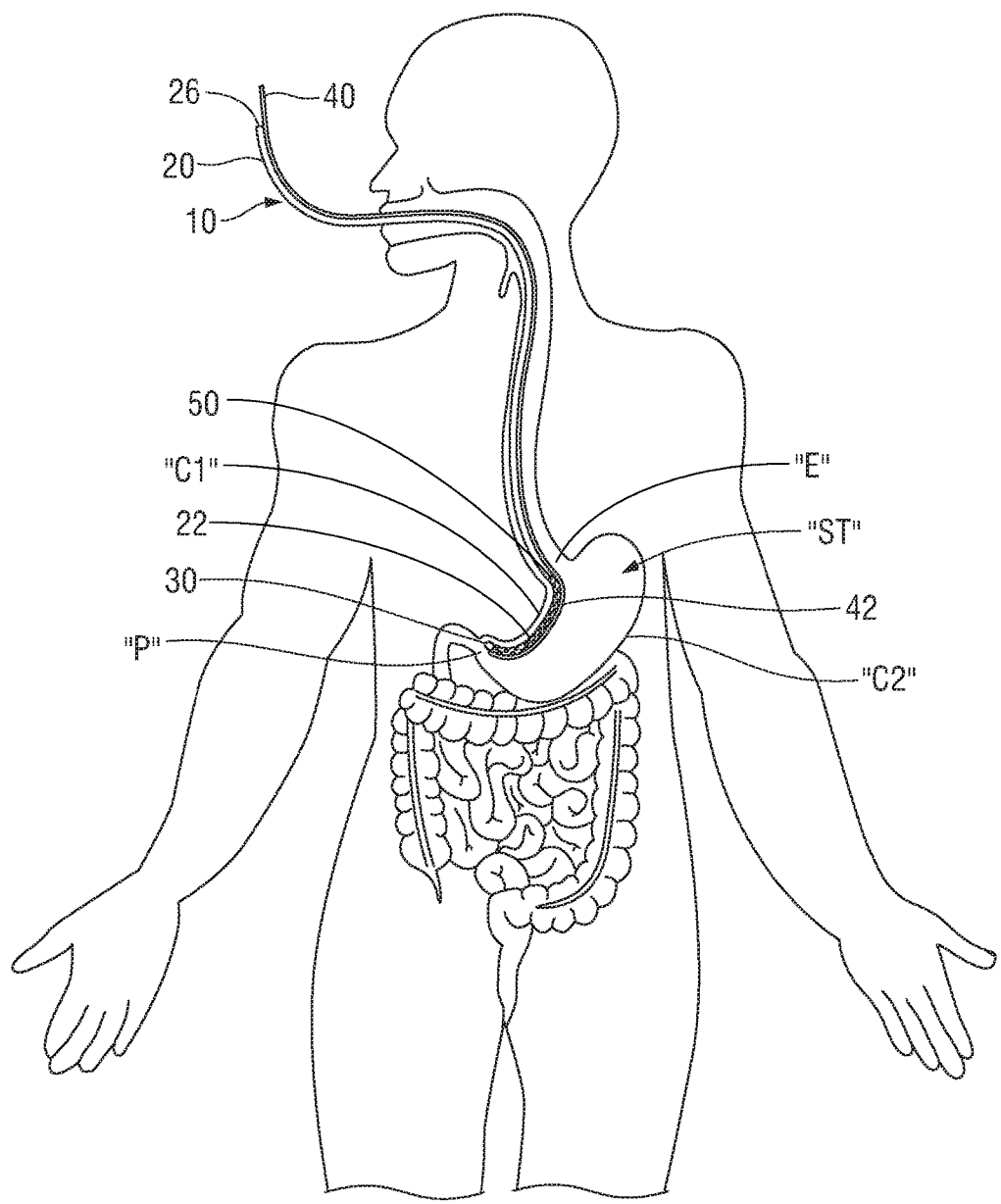
FIG. 1 is a schematic illustration showing a device provided in accordance with the present disclosure inserted into a patient's stomach.

Embodiments of the present disclosure are detailed below with reference to the drawings in which like reference numerals designate identical or corresponding elements in each of the several views. Throughout this description, the term "proximal" will refer to the portion of the device or component thereof that is closest to the user and the term "distal" will refer to the portion of the device or component thereof that is farthest from the user.

Figure 2:
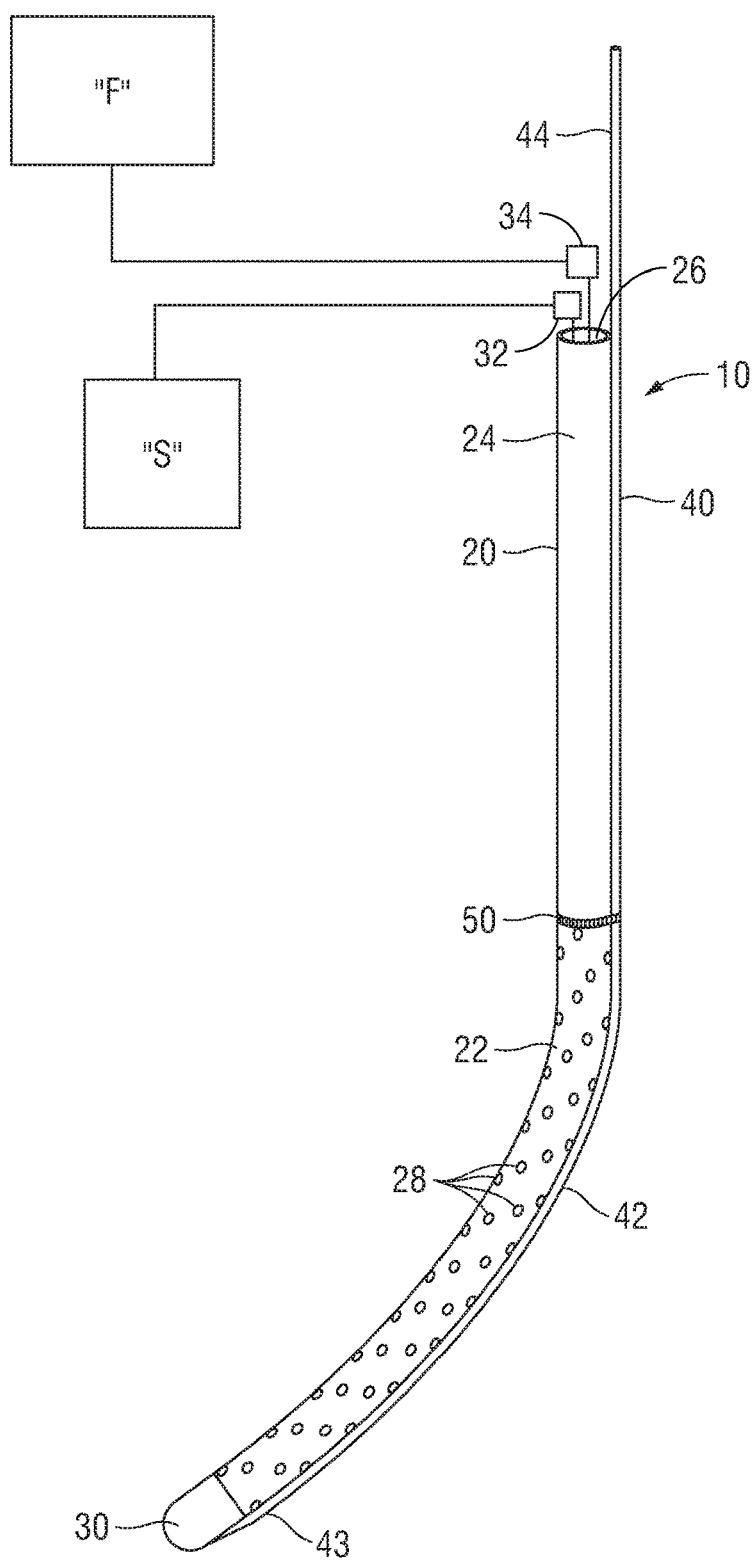
FIG. 2 is a perspective view of a system provided in accordance with the present disclosure including the device of FIG. 1 disposed in a first condition.
Figure 3:
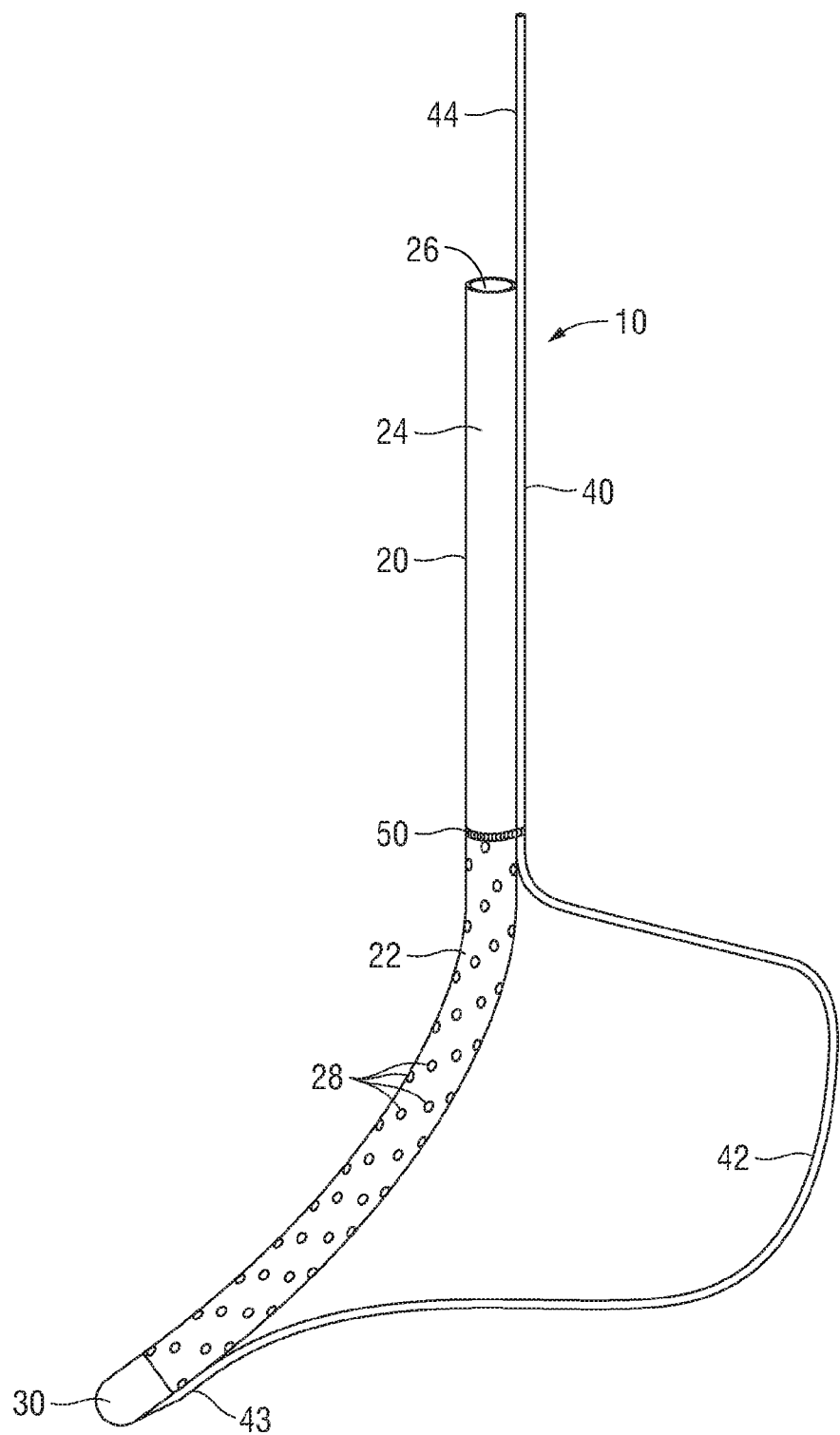
FIG. 3 is a perspective view of the device of FIG. 1, disposed in a second condition.

Turning now to FIGS. 1-3, a device provided in accordance with the present disclosure and configured for use during a sleeve gastrectomy procedure is shown generally identified by reference numeral 10. As best shown in FIGS. 2-3, device 10 includes an elongated tube member 20 and an elongated rod member 40 coupled to tube member 20. The materials for the tube member 20 and the rod member are generally polymeric materials appropriate for surgical applications, such as the materials used to make a bougie or catheter. The tube member is hollow, whereas the rod member can be hollow or solid. Tube member 20 is formed from flexible materials such as silicone and rubber, although other suitable flexible materials are also contemplated. Tube member 20 has a distal portion 22 and a proximal portion 24 and defines a lumen 26 extending therethrough. A plurality of perforations or apertures 28 are defined through an outer wall of distal portion 22 of tube member 20. Apertures 28 enable fluid communication through the outer wall of tube member 20 between lumen 26 and the exterior of tube member 20. Tube member 20 further includes a distal end cap 30. The distal end of the tubular member 20 is closed in any appropriate manner. Distal end cap 30 may define a rounded tapered configuration, blunt conical configuration, or any other suitable configuration that facilitates atraumatic insertion into a patient's stomach "ST" (FIG. 1). Distal end cap 30 is affixed to the distal end of tube member 20 in sealing engagement therewith to seal off lumen 26 at the distal end of tube member 20.

Tube member 20 is configured to connect to a suction source "S" and a fluid source "F." Suction source "S" is operable to provide suction within lumen 26 for suctioning fluids, stomach contents, etc. through apertures 28 and into lumen 26 for removal and/or for suctioning stomach tissue into contact with tube member 20. One or more control members 32, e.g., a valve, may interdisposed between tube member 20 and the suction source "S" to control the suction force being applied, although controls may alternatively or additionally provided on a user interface (not shown) of the suction source "S." Fluid source "F" is configured to pump fluid, e.g., water or air, into lumen 26 of tube member 20 and out through apertures 28 into the stomach "ST" (FIG. 1). Similar to suction source "S," the fluid source "F" may include one or more control members 34, e.g., a valve, interdisposed between tube member 20 and the fluid source "F" to control the flow rate and/or pressure of fluid being pumped through lumen 26 of tube member 20, although controls may alternatively or additionally provided on a user interface (not shown) of the fluid source "F." The tube member 20 can have one or more passageways.

Continuing with reference to FIGS. 2-3, rod member 40 is formed from a semi-rigid, resiliently flexible material, e.g., a suitable elastomer, and defines a length greater than the length of tube member 20 such that rod member 40 can be accessed outside the patient and/or remotely of the surgical site. Rod member 40 defines a distal portion 42 having a distal end 43 and a proximal portion 44. Distal end 43 of rod member 40 is integrally, i.e., monolithically, formed with or otherwise affixed to distal end cap 30. A coupling 50, e.g., a ring, sleeve, hook, latch, etc., affixed to tube member 20 slidably receives a portion of rod member 40 therethrough to slidably couple rod member 40 to tube member 20 intermediate the distal and proximal portions 22, 24, respectively, of tube member 20. As a result of the above-configuration, rod member 40 is slidable through coupling 50 and relative to tube member 20 between a contracted position corresponding to a first condition of device 10 (FIG. 2), wherein distal portion 42 of rod member 40 extends along and abuts the outer surface of tube member 20 is substantially parallel relation relative thereto, and a deployed position corresponding to a second condition of device 10 (FIG. 3), wherein distal portion 42 of rod member 40 is bowed outwardly from tube member 20 and is spaced therefrom. In the deployed position, rod member 40 defines a configuration that generally complements the curvature of the greater curvature portion "C2" of the stomach "ST" (FIG. 1). Preferably, the flexibility and resilience and dimensioning of the member 40 is such that member 40 automatically forms a half-heart shape, with a large, bowed, curvature adjacent the proximal portion 44. Such a shape complements the greater curvature of the stomach. These features can be adapted to applications in other hollow organs as well. The rod member should be strong enough to stretch out the stomach, and reposition the anterior and posterior walls of the stomach. Proximal portion 44 of rod member 40 may be grasped and manipulated relative to tube member 20 to transition rod member 40 between the contracted and deployed positions. As mentioned above, rod member 40 is dimensioned such that proximal portion 44 is accessible from outside the patient, thus readily enabling manipulation thereof. More specifically, translating rod member 40 distally relative to tube member 20 and coupling 50 urges rod member 40 distally through coupling 50 such that distal portion 42 of rod member 40 is bowed outwardly relative to tube member 20 towards the deployed position. Translating rod member 40 proximally relative to tube member 20 pulls rod member 40 proximally through coupling 50 such the distal portion 42 of rod member 40 is pulled inwardly relative to tube member 20 towards the contracted position. As an alternative to manually manipulating rod member 40, an actuator or actuation assembly (not shown) may be coupled to the proximal ends of tube member 20 and rod member 40 to enable selective translation of rod member 40 relative to tube member 20.

Figure 4:
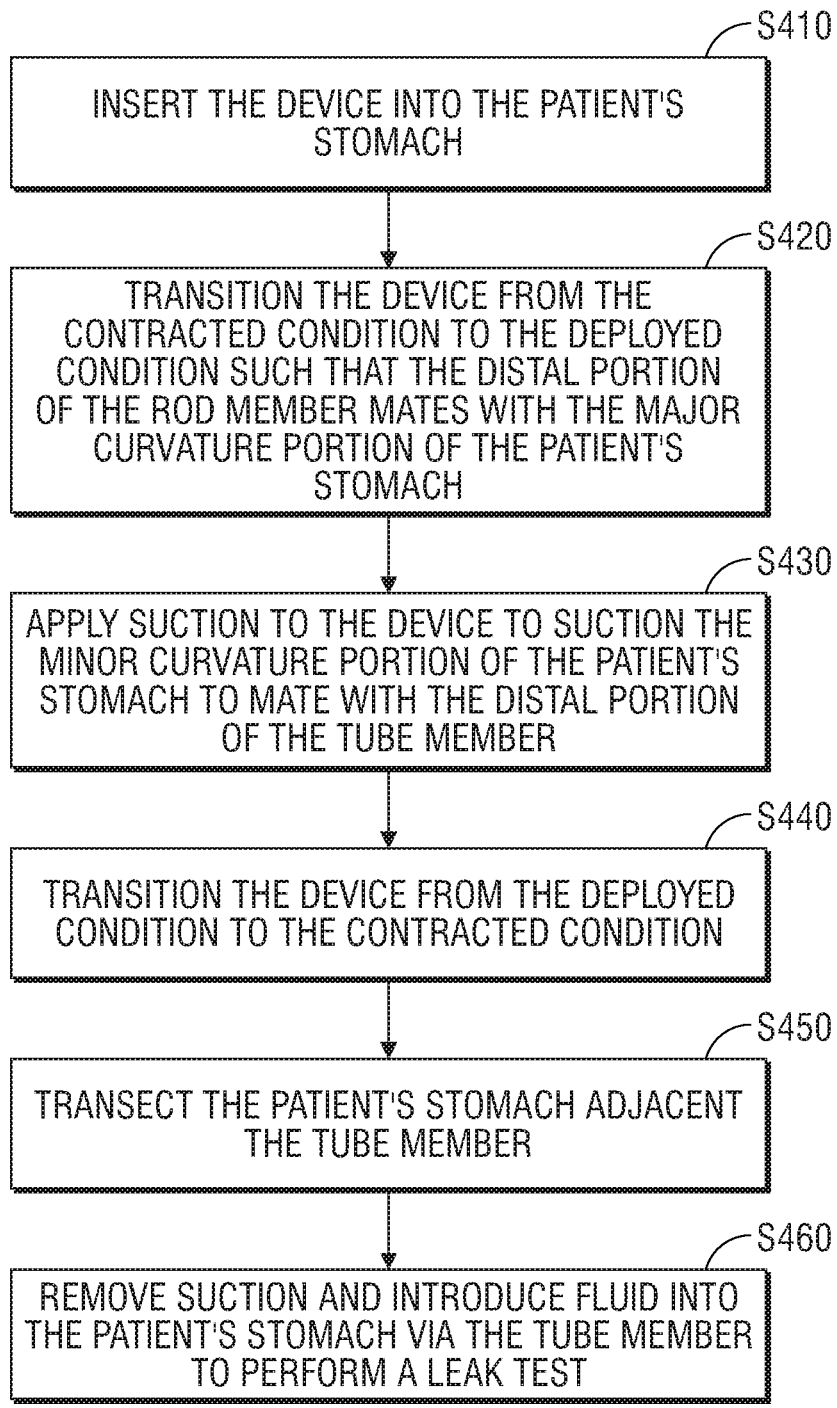
FIG. 4 is a flow diagram illustrating a method of performing a bariatric surgical procedure provided in accordance with the present disclosure.

Referring to FIG. 4, in conjunction with FIGS. 1-3, the use of device 10 during the course of a sleeve gastrectomy procedure is described. However, it is also envisioned that device 10 be capable of use in other similar surgical procedures, within hollow organs other than the stomach, etc. Initially, with rod member 40 disposed in the contracted condition, device 10, lead by distal end cap 30, is inserted through the patient's mouth, esophagus, and into the patient's stomach "ST" to the position shown in FIG. 1, wherein at least distal portion 22 of tube member 20, coupling 50, and distal portion 42 of rod member 40 are disposed within the patient's stomach "ST" (step S410). Once this position has been achieved, proximal portion 44 of rod member 40 is translated distally relative to tube member 20 such that distal portion 42 of rod member bows outwardly relative to tube member 20 towards the deployed position. As distal portion 42 of rod member 40 bows outwardly towards the deployed position, tube member 20 is urged towards and into complementary mating relation with the lesser curvature portion "C1" of the stomach "ST," while distal portion 42 of rod member 40 is urged towards and into complementary mating relation with the greater curvature portion "C2" of the stomach "ST" (step S420), engaging and flattening the stomach. As such, the orientation of device 10 with tube member 20 extending along the lesser curvature portion "C1" of the stomach "ST" between the esophageal sphincter "E" and the pyloric sphincter "P" can be readily achieved. As a result of this configuration of device 10 in the second condition, the above-described orientation of device 10 within the stomach is maintained despite spasms, folding, spiraling, and/or shifting of the stomach "ST." Further, the configuration of device 10 allows for proper positioning within the stomach "ST" without the assistance of an viewing instrument, e.g., an endoscope (not shown).

Once the proper orientation of tube member 20 of device 10 has been achieved, suction source "S" may be activated to apply suction within lumen 26 for suctioning any remaining contents within the stomach "ST" into lumen 26 of tube member 20 through apertures 28. Application of suction within lumen 26 also suctions the lesser curvature portion "C1" of the stomach "ST" to the outer periphery of tube member 20, to ensure and maintain the complementary mating relation of tube member 20 with the lesser curvature portion "C1" of the stomach "ST" (step S430). Control member 32 may be manipulated or otherwise controlled to apply sufficient suction to maintain the relative position of tube member 20 without damaging surrounding tissue.

With tube member 20 maintained in position relative to the lesser curvature portion "C1" of the stomach "ST" as a result of the applied suction, proximal portion 44 of rod member 40 is translated proximally relative to tube member 20 such the distal portion 42 of rod member 40 is pulled inwardly relative to tube member 20 back to the contracted position (step S440). As suction is maintained at this point, tube member 20 is maintained in the positioned detailed above despite contraction of distal portion 42 of rod member 40.

Once distal portion 42 of rod member 40 has been returned to the contracted position, transection of the stomach "ST" adjacent tube member 20 on a opposite side of tube member 20 relative to the lesser curvature portion "C1" of the stomach "ST" may be effected in any suitable fashion (step S450), e.g., using a stapling device or other suitable device. Transection in this manner reforms the stomach "ST" to a tubular-shaped configuration that slightly larger than the outer dimension of tube member 20 and extends between the esophageal sphincter "E" and the pyloric sphincter "P." The suction is maintained while the stomach tissue is transected and stapled, the shape of the tube member 20 forming a visible bulge. As can be appreciated, the diameter of tube member 20 may be selected in accordance with a desired diameter of the tubular-shape reformed stomach. The remaining stomach tissue is removed from the patient.

Upon completion of the stomach transection, the applied suction is removed and a leak test is performed (step S460). The leak test is performed by activating the fluid source "F" to pump fluid through lumen 26 of tube member 20 and into the stomach via apertures 28. The fluid may be air, colored water, or other suitable gaseous or liquid leak test agent. The fluid is pumped into the stomach "ST," e.g., via controlling control member 34, to achieve a pressure within the stomach "ST" sufficient to test the transected stomach tissue for extravasation. If extravasation is detected, the leak is repaired prior to completing the procedure, by suturing or any other appropriate method. The leak test is repeated after repairing the portion or portions of transected tissue where extravasation is detected, until no further extravasation is detected. Ultimately, device 10 is withdrawn from the patient's stomach "ST." A scope can be provided with the device, and the tube member may have a separate passageway for the scope or other devices. Alternatively, the user of the device may pass a scope through the singular passageway as needed.

In any of the embodiments disclosed herein, the tube member can be made of a clear polymer and a scope or camera is provided. In any of the embodiments disclosed herein, an ultrasound probe can be provided.

In any of the embodiments disclosed herein, the rod member 40 can be detachable from the tube member 20. The attachment or connection at the distal end of the tube member 20 can be frangible, releasable, etc., to allow the rod member 40 to be detached from the tube member 20. In this way, the user of the device has removed the rod member 40 from the site, while maintaining the position of the stomach (using suction, as discussed, avoiding transecting or stapling the rod member 40.

It will be understood that various modifications may be made to the embodiments of the present disclosure herein. Therefore, the above description should not be construed as limiting, but merely as exemplifications of embodiments. Those skilled in the art will envision other modifications within the scope and spirit of the present disclosure.

What is claimed is:

1. A method of bariatric surgery, comprising:
   inserting a device at least partially into a patient's stomach, the device including:
   an elongated flexible tube member defining a proximal portion and a distal portion having a distal end; and
   an elongated resilient rod member defining a proximal portion and a distal portion having a distal end, the rod member slidably coupled to the tube member intermediate the proximal and distal portions of the tube member, the distal end of the rod member fixedly coupled to the distal end of the tube member;
   positioning the flexible tube member along a lesser curvature portion of the patient's stomach;
   transitioning the device from a contracted condition to a deployed condition wherein, in the deployed condition, a portion of the rod member bows outwardly relative to the tube member to follows a greater curvature portion of the patient's stomach;
   applying suction to retain the lesser curvature portion of the patient's stomach against the flexible tube member, while flattening the greater curvature portion of the patient's stomach;
   transitioning the device from the deployed condition back to the contracted condition; and
   transecting the patient's stomach adjacent the tube member.

2. The method according to claim 1, wherein the proximal portion of the rod member is translated distally relative to the tube member to transition the device from the contracted condition to the deployed condition.

3. The method according to claim 2, wherein the proximal portion of the rod member is translated proximally relative to the tube member to transition the device from the deployed condition back to the contracted condition.

4. The method according to claim 1, further comprising stapling anterior and posterior sides of the stomach together to form a tubular shape.

5. The method according to claim 4, further including introducing fluid through the tube member and into the patient's stomach to perform a leak test, after the stomach is transected and stapled.

6. The method according to claim 1, wherein the application of the suction fixes anterior and posterior sides of the stomach to one another and prevents movement of the anterior and posterior sides while the stomach is transected by a surgeon, the suction allowing for clear identification of the tube member.

\* \* \* \* \*